(12) United States Patent
King et al.

(10) Patent No.: US 7,875,724 B2
(45) Date of Patent: Jan. 25, 2011

(54) REGIOSPECIFIC SYNTHESIS OF NICOTINE DERIVATIVES

(75) Inventors: Laura S. King, Wilmington, NC (US); Emilie Smith, Durham, NC (US); Daniel L. Comins, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/687,952

(22) Filed: Jan. 15, 2010

(65) Prior Publication Data

US 2010/0113785 A1 May 6, 2010

Related U.S. Application Data

(62) Division of application No. 11/924,644, filed on Oct. 26, 2007, now Pat. No. 7,671,209, which is a division of application No. 11/463,986, filed on Aug. 11, 2006, now Pat. No. 7,304,160, which is a division of application No. 10/715,147, filed on Nov. 17, 2003, now Pat. No. 7,112,678.

(51) Int. Cl.
*C07D 401/04* (2006.01)
(52) U.S. Cl. .................. 546/279.4; 549/268.1
(58) Field of Classification Search ............... 546/268.1, 546/279.4

See application file for complete search history.

(56) References Cited

U.S. PATENT DOCUMENTS

| | | | |
|---|---|---|---|
| 4,855,433 | A | 8/1989 | Zeldin et al. |
| 5,594,011 | A | 1/1997 | McDonald et al. |
| 5,723,477 | A | 3/1998 | McDonald et al. |
| 6,995,265 | B2 | 2/2006 | Comins et al. |

FOREIGN PATENT DOCUMENTS

WO  WO 92/12975  8/1992

OTHER PUBLICATIONS

Seeman Ji et al. Steric and conformational effects in nicotine chemistry. The Journal of Organic Chemistry. 1981; 46(15): 3040-3048.
Hoffman RV. Organic Chemistry: An intermediate text, second edition. 2004: 124-144. John Wiley & Sons, Hoboken, NJ.
Notification of Transmittal of the International Search Report for international application PCT/US03/37655. Mailed May 12, 2004.
Bleicher et al., A Practical and Efficient Synthesis of the Selective Neuronal Acetylcholine-Gated Ion Channel Agonist (S)-(−)-5-Ethynyl-3-)1-methyl-2-pyrrolidinyl) pyridine Maleate, *J. Org. Chem.*, 63:1109-1118 (1998).
Brown et al., A Convenient Synthesis of Dimethyl (Diazomethyl) phosphonate (Seyferth/Gilgert Reagent), *J. Org. Chem.*, 61:2540-2541 (1996).
Despagnet et al., Synthesis of Nicotine Derivatives from Nicotine, *ACS Southeast Regional Meeting Abstract*, Aug. 27, 2003.
Gros et al., Lithiation of 2-Heterosubstituted Pyridines with BuLi-LiDMAE: Evidence for Regiospecificity at C-6, *J. Org. Chem.*, 67:234-237 (2002).
Dehn et al., Nicotine and Cotinine Adducts of Melanin Intermediate Demonstrated by Matrix-Assisted Laser Desorption/Ionization Time-of-Flight Mass Spectrometry, *Chemical Research in Toxicology*, 14(3):275-279 (2001).
Wang et al., Structure-activity relationships for nicotine analogs comparing competition for [3H]nicotine binding and psychotropic potency, Drug Development Research, 45(1):10-16 (1998).
Seeman et al., Preparation of Hydroxyalkyl-Substituted Nicotinoids, J. Org. Chem., 51(9):1548-1551 (1986).
Seeman et al., Organometallic Methylation of Nicotine and Nicotine N-Oxide, Reaction Pathways and Racemization Mechanisms, J. Orl. Chem. 48(25):4899-4904 (1983).
Supplemental European Search Report, EP 03 79 0030, Jul. 3, 2008.
Seeman Ji et al. Nicotine chemistry. The addition of alkyl radicals to (S)-(−)-nicotine: synthesis of optically active 6-alkylnicotines. Synthesis. 1985; 1985(10): 953-955.
Armstrong DW et al. Capillary gas chromatographic separation of enantiomers with stable dipentyl-α-, β- and γ-cyclodextrin-derivatized stationary phases. Analytica Chemica Acta. 1990; 234: 365-380.

*Primary Examiner*—Golam M. M. Shameem
*Assistant Examiner*—Samantha L Shterengarts
(74) *Attorney, Agent, or Firm*—Myers Bigel Sibley & Sajovec, P.A.

(57) ABSTRACT

Methods of synthesizing nicotine analogs and derivatives are described. The methods are particularly useful for the regioselective production of enantiomerically pure nicotine analogs having substituents at the C4 position. Intermediates useful for the synthesis of such compounds are also described.

4 Claims, No Drawings

REGIOSPECIFIC SYNTHESIS OF NICOTINE DERIVATIVES

RELATED APPLICATIONS

This application is a divisional of U.S. patent application Ser. No. 11/924,644, filed Oct. 26, 2007, now U.S. Pat. No. 7,671,209, which is a divisional of U.S. patent application Ser. No. 11/463,986, filed Aug. 11, 2006, now U.S. Pat. No. 7,304,160, which is a divisional of U.S. patent application Ser. No. 10/715,147, filed Nov. 17, 2003, now U.S. Pat. No. 7,112,678, the disclosure of each of which is incorporated herein by reference in its entirety.

FIELD OF THE INVENTION

The present invention concerns methods and intermediates useful for the regiospecific synthesis of compounds active for modulating nicotinic acetylcholine receptors.

BACKGROUND OF THE INVENTION

Acetylcholine receptors are involved in the modulation of a variety of physiological and behavioral functions, including neuroendocrine function, respiration, mood, motor control and function, focus and attention, concentration, memory and cognition, and substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, is widespread in the brain. In the periphery, acetylcholine receptors are found in muscle, autonomic ganglia, the gastrointestinal tract and the cardiovascular system (see, e.g., U.S. Pat. No. 5,594,011).

Acetylcholine receptors have been shown to be decreased, among other things, in the brains of patients suffering from Alzheimer's disease, and Parkinson's disease, as well as diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. U.S. Pat. No. 5,594,011 to McDonald et al., assigned to SIBIA Neuroscience, describes compounds such as SIB-1508Y that modulate nicotinic acetylcholine receptors. Such compounds are useful for, among other things, the treatment of Parkinson's disease. See also U.S. Pat. No. 5,723,477 to McDonald et al. Unfortunately, nicotine analogs are difficult compounds to synthesize, and there is a continuing need for new methods of making the same, as well as intermediates useful for the synthesis of nicotine analogs.

SUMMARY OF THE INVENTION

In general, the present invention provides regiospecific methods for the production of enantiomerically pure nicotine analogs bearing substituents other than hydrogen at the C4 position.

Accordingly, a first aspect of the present invention is a regiospecific method of making a compound of Formula I:

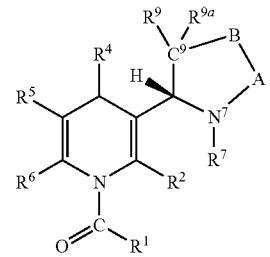

(I)

wherein:

$R^4$ is alkyl, alkenyl, alkynyl, aryl or $SiR^{20}R^{21}R^{22}$, wherein $R^{20}$, $R^{21}$ and $R^{22}$ are each independently selected from the group consisting of alkyl, alkenyl, alkynyl and aryl;

$R^1$ is alkyl, aryl, alkenyl, alkynyl, alkoxy, —$NR''_2$ or —$SR''$, where $R''$ is alkyl, aryl, alkenyl, alkynyl, or alkoxy;

$R^2$, $R^5$, and $R^6$ are each independently selected from the group consisting of H, alkyl, aryl, alkenyl, alkynyl, alkoxy, and halo;

$R^7$ is selected from the group consisting of consisting of H and alkyl;

A is a 1, 2 or 3 atom bridging species which forms part of a saturated or monounsaturated 5-, 6- or 7-membered ring including $N^7$, $C^8$, $C^9$ and B;

B is selected from —O—, —S—, —$NR^{10}$—, wherein $R^{10}$ is selected from hydrogen, alkyl, aryl, substituted aryl, alkylaryl, substituted alkylaryl, arylalkyl, substituted arylalkyl; —$C^{10}HR^{10a}$, wherein $R^{10a}$ is selected from hydrogen, alkyl, hydroxyalkyl, aryl, aryloxyalkyl, fluoro, trifluoromethyl, cyano, cyanomethyl, —OR', —$NR'_2$, or —SR', wherein each R' is independently hydrogen, alkyl, alkenyl, alkynyl or aryl, provided, however, that neither the —$NR'_2$ nor the —SR' functionality is conjugated with an alkenyl or alkynyl functionality; or B is =$C^{10}R^{10a}$ or =N—, preferably provided there is no double bond in the ring between A and B, or between B and $C^9$ when there is a double bond between $N^7$ and $C^8$, and preferably provided that B is not a heteroatom when A is a 1 atom bridging species; and $R^9$ and $R^{9a}$ are each independently selected from hydrogen, alkyl, hydroxyalkyl, aryl, aryloxyalkyl, fluoro, trifluoromethyl, cyano, cyanomethyl, —OR', —$NR'_2$, or —SR', wherein each R' is as defined above, preferably provided, however, that neither the —$NR'_2$ nor the —SR' functionality is conjugated with an alkenyl or alkynyl functionality; comprising:

reacting an organometallic nucleophile $R^4$Met, where $R^4$ is as given above and Met is a metal, with a compound of the formula:

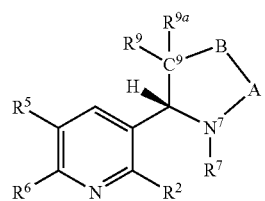

wherein A, B, $R^2$, $R^5$, $R^6$, $R^7$, $R^9$, and $R^{9a}$ are as given above, and a compound of the formula $R^1COX^1$, wherein $R^1$ is as given above and $X^1$ is halo, to produce a compound of Formula I.

A second aspect of the present invention is a compound of Formula I:

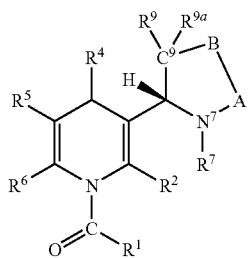

(I)

wherein:

A, B, $R^1$, $R^2$, $R^4$, $R^5$, $R^6$, $R^7$, $R^9$, and $R^{9a}$ are as described above. Optionally but preferably the compound is enantiomerically pure.

A further aspect of the present invention is a method of making a compound of Formula II:

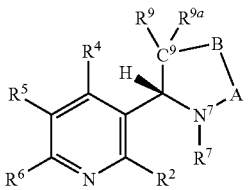

(II)

wherein A, B, $R^2$, $R^4$, $R^5$, $R^6$, $R^7$, $R^9$, and $R^{9a}$ are as described above;

comprising oxidizing a compound of Formula I:

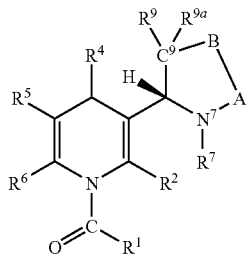

(I)

wherein A, B, $R^1$, $R^2$, $R^4$, $R^5$, $R^6$, $R^7$, $R^9$, and $R^{9a}$ are as given above to produce a compound of Formula II.

A further aspect of the present invention is an enantiomerically pure C4-substituted nicotine analog produced by the method described above (i.e., a compound of Formula II). An example of a particular embodiment is an enantiomerically pure compound of Formula II:

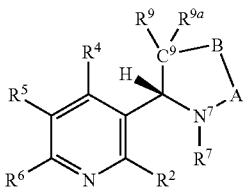

(II)

wherein $R^4$ is as described above; and A, B, $R^2$, $R^5$, $R^6$, $R^7$, $R^9$, and $R^{9a}$ are as described above; subject to the proviso that $R^4$ is different from at least one of (and in some embodiments all of) $R^2$, $R^5$ and $R^6$. Another embodiment is an enantiomerically pure compound of Formula II:

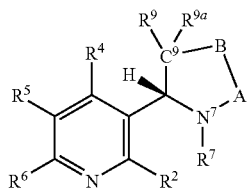

(II)

wherein $R^4$ is $SiR^{20}R^{21}R^{22}$, wherein $R^{20}$, $R^{21}$ and $R^{22}$ are as given above; and A, B, $R^2$, $R^5$, $R^6$, $R^7$, $R^9$, and $R^{9a}$ are as described above.

A further aspect of the present invention is a method of making a compound of Formula III:

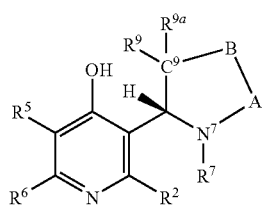

(III)

wherein:

A, B, $R^2$, $R^5$, $R^6$, $R^7$, $R^9$, and $R^{9a}$ are as described above; comprising oxidizing a compound of Formula II:

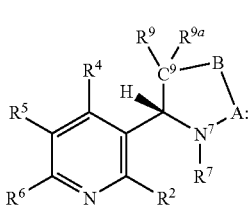

(II)

wherein A, B, R, $R^2$, $R^5$, $R^6$, $R^7$, $R^9$, and $R^{9a}$ are as given above, and $R^4$ is $SiR^{20}R^{21}R^{22}$, wherein $R^{20}$, $R^{21}$ and $R^{22}$ are each independently selected from the group consisting of alkyl alkenyl, alkynyl and aryl in a polar protic solvent to produce a compound of Formula III.

A still further aspect of the present invention is an enantiomerically pure compound of Formula III as described above.

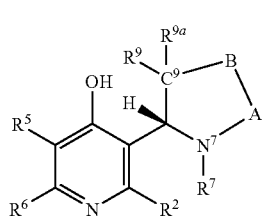

(III)

The foregoing and other objects and aspects of the present invention are explained in greater detail below.

DETAILED DESCRIPTION OF THE PREFERRED EMBODIMENTS

"Alkyl" as used herein refers to straight or branched chain alkyl groups having in the range of about 1 up to 12, 20, or 30 carbon atoms. In some embodiments the alkyl can be a lower alkyl. "Lower alkyl" refers to straight or branched chain alkyl radicals having in the range of about 1 up to 6 carbon atoms. Alkyl and lower alkyl may be substituted or unsubstituted unless specified otherwise herein; "substituted alkyl" refers to alkyl, cycloalkyl or lower alkyl groups further bearing one or more substituents such as hydroxy, alkoxy (of a lower alkyl group), aryl, mercapto (of a lower alkyl group), halogen, trifluoromethyl, cyano, nitro, amino, carboxyl, carbamate, sulfonyl, silyl, sulfonamide, and the like. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, cyclohexyl, and the like.

"Alkoxy" as used herein refers to a compound of the formula RO—, where R is alkyl or lower alkyl (which may be substituted or unsubstituted unless specified otherwise) as given above.

"Alkenyl" refers to straight or branched chain hydrocarbyl groups such as alkyl or lower alkyl groups as described above (and which may be substituted or unsubstituted unless specified otherwise) and having at least one carbon-carbon double bond.

"Alkynyl" refers to straight or branched chain hydrocarbyl groups such as alkyl or lower alkyl groups as described above (and which may be substituted or unsubstituted unless specified otherwise) and having at least one carbon-carbon triple bond.

"Aryl," as used herein, refers to a monocyclic carbocyclic or heterocyclic ring system or a bicyclic carbocyclic or heterocyclic fused ring system having one or more aromatic rings. Examples of aryl include but are not limited to azulenyl, indanyl, indenyl, naphthyl, phenyl, tetrahydronaphthyl, and the like. The aryl groups may be substituted or unsubstituted unless specified otherwise and when substituted can for example be substituted with 1, 2, 3, 4, or 5 substituents independently selected from alkyl, alkenyl, alkenyloxy, alkoxy, alkoxyalkoxy, alkoxycarbonyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Organometallic nucleophile" are generally expressed as $R^4$Met, where Met is a suitable metal such as magnesium, manganese, lithium, sodium, copper, cerium, zinc, cadmium, aluminum or titanium. Additional groups $R^4$ may optionally be present and a halide may optionally be present as is known in the art. Suitable organometallic nucleophiles include Grignard reagents.

"Grignard reagent" as used herein refers to an organomagnesium halides, $R^4$MgX, having a carbon-magnesium or silicon-magnesium bond (or their equilibrium mixtures in solution with $R^4{}_2$Mg+MgX$_2$), wherein $R^4$ is a hydrocarbyl or silyl group such as alkyl, alkenyl, alkynyl or aryl, or a corresponding silyl group.

"Halo" refers to fluoro, chloro, bromo or iodo.

The disclosures of all United States patent references cited herein are to be incorporated herein by reference in their entirety.

Starting materials for the reactions described herein include both nicotine and nicotine analogs and derivatives, including analogs substituted at the 2, 5 and 6 position, including but not limited to those described in U.S. Pat. Nos. 5,594,011 and 5,723,477 (including both novel compounds described therein and known compounds described therein). Examples of such starting materials are illustrated by Formulas i-ii below:

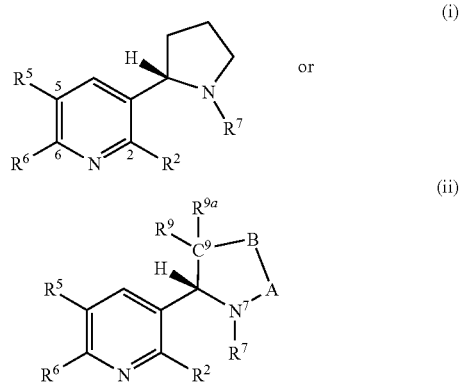

wherein:

$R^2$, $R^5$, and $R^6$ are each independently selected from the group consisting of H, alkyl, aryl, alkenyl, alkynyl, alkoxy, and halo, preferably H or alkyl (e.g. methyl);

$R^7$ is selected from the group consisting of H and alkyl (e.g., methyl);

A is a 1, 2 or 3 atom bridging species which forms part of a saturated or monounsaturated 5-, 6- or 7-membered ring including $N^7$, $C^8$, $C^9$ and B;

B is selected from —O—, —S—, —NR$^{10}$—, wherein R$^{10}$ is selected from hydrogen, alkyl, aryl, substituted aryl, alkylaryl, substituted alkylaryl, arylalkyl, substituted arylalkyl; —C$^{10}$HR$^{10a}$—, wherein R$^{10a}$ is selected from hydrogen, alkyl, hydroxyalkyl, aryl, aryloxyalkyl, fluoro, trifluoromethyl, cyano, cyanomethyl, —OR', —NR'$_2$, or —SR', wherein each R' is independently hydrogen, alkyl, alkenyl, alkynyl or aryl, preferably provided, however, that neither the —NR'$_2$ nor the —SR' functionality is conjugated with an alkenyl or alkynyl functionality; or B is =C$^{10}$R$^{10a}$ or =N—, preferably provided there is no double bond in the ring between A and B, or between B and C$^9$ when there is a double bond between N$^7$ and C$^8$, and preferably provided that B is not a heteroatom when A is a 1 atom bridging species; and $R^9$ and $R^{9a}$ are each independently selected from hydrogen, alkyl, hydroxyalkyl, aryl, aryloxyalkyl, fluoro, trifluoromethyl, cyano, cyanomethyl, —OR', —NR'$_2$, or —SR', wherein each R' is as defined above, preferably provided, however, that neither the —NR'$_2$ nor the —SR' functionality is conjugated with an alkenyl or alkynyl functionality.

As noted above, a first aspect of the present invention is a regiospecific method of making a compound of Formula I:

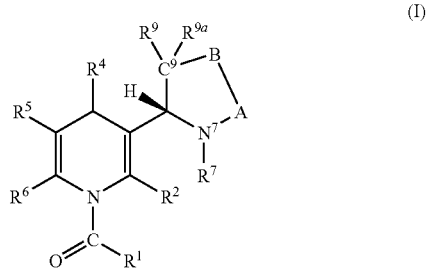

wherein:

$R^4$ is alkyl, alkenyl, alkynyl, aryl or $SiR^{20}R^{21}R^{22}$, wherein $R^{20}$, $R^{21}$ and $R^{22}$ are each independently selected from the group consisting of alkyl, alkenyl, alkynyl and aryl;

$R^1$ is alkyl, aryl, alkenyl, alkynyl, alkoxy, $-NR''_2$ or $-SR''$, where $R''$ is alkyl, aryl, alkenyl, alkynyl, or alkoxy;

$R^2$, $R^5$, and $R^6$ are each independently selected from the group consisting of H, alkyl, aryl, alkenyl, alkynyl, alkoxy, and halo;

$R^7$ is selected from the group consisting of consisting of H and alkyl;

A is a 1, 2 or 3 atom bridging species which forms part of a saturated or monounsaturated 5-, 6- or 7-membered ring including $N^7$, $C^8$, $C^9$ and B;

B is selected from $-O-$, $-S-$, $-NR^{10}-$, wherein $R^{10}$ is selected from hydrogen, alkyl, aryl, substituted aryl, alkylaryl, substituted alkylaryl, arylalkyl, substituted arylalkyl; $-C^{10}HR^{10a}-$, wherein $R^{10a}$ is selected from hydrogen, alkyl, hydroxyalkyl, aryl, aryloxyalkyl, fluoro, trifluoromethyl, cyano, cyanomethyl, $-OR'$, $-NR'_2$, or $-SR'$, wherein each $R'$ is independently hydrogen, alkyl, alkenyl, alkynyl or aryl, provided, however, that neither the $-NR'_2$ nor the $-SR'$ functionality is conjugated with an alkenyl or alkynyl functionality; or B is $=C^{10}R^{10a}$ or $=N-$, preferably provided there is no double bond in the ring between A and B, or between B and $C^9$ when there is a double bond between $N^7$ and $C^8$, and preferably provided that B is not a heteroatom when A is a 1 atom bridging species; and $R^9$ and $R^{9a}$ are each independently selected from hydrogen, alkyl, hydroxyalkyl, aryl, aryloxyalkyl, fluoro, trifluoromethyl, cyano, cyanomethyl, $-OR'$, $-NR'_2$, or $-SR'$, wherein each $R'$ is as defined above, preferably provided, however, that neither the $-NR'_2$ nor the $-SR'$ functionality is conjugated with an alkenyl or alkynyl functionality.

The method comprises reacting an organometallic nucleophile $R^4Met$, where $R^4$ is as given above and Met is a metal, with a nicotine or nicotine analog starting material such as a compound of the formula (I) or (ii) as given above, and a compound of the formula $R^1COX^1$, wherein $R^1$ is as given above and $X^1$ is halo, to produce a compound of Formula I. In some embodiments the organometallic nucleophile is a Grignard reagent. Grignard reagents suitable for carrying out the present invention can be prepared in accordance with known techniques, including but not limited to those described in U.S. Pat. Nos. 6,617,282; 6,608,212; 6,603,000; 6,600,040; 6,593,471; 6,590,125; 6,590,125; 6,590,103; 6,579,993; 6,570,107; 6,569,799; etc. In general, Grignard reagents may be prepared from magnesium which may be in the form of magnesium granules, magnesium turnings, magnesium dust, magnesium powder, suspension of magnesium in oil, and the like. To minimize safety risks, the use of magnesium granules is preferred. Preferred solvents for preparing the Grignard reagent comprise an organic solvent such as toluene, tetrahydrofuran (THF), diethyl ether, diglyme, methyl t-butyl ether, and mixtures thereof. The time and temperature of the reaction is not critical, but in general the reaction may be carried out from 1-24 hours at a low temperature (e.g., between −100 and 0° C.) in a suitable solvent such as tetrahydrofuran, toluene, or an ether solvent, until the reaction is quenched by addition of a suitable quenching agent such as water or aqueous ammonium chloride. Compounds of Formula I produced by such methods are optionally but preferably enantiomerically pure, and may optionally but in some embodiments preferably bear a group $R^4$ that is different from at least one, or all of, groups $R^2$, $R^5$, and $R^7$. In some embodiments, $R^4$ is alkyl, alkenyl, alkynyl, or aryl. In some embodiments, $R^4$ is $SiR^{20}R^{21}R^{22}$, and wherein $R^{20}$, $R^{21}$ and $R^{22}$ are each independently selected from the group consisting of alkyl alkenyl, alkynyl and aryl. In some embodiments, $R^1$ is alkyl.

A further aspect of the present invention, as also noted above, is a method of making a compound of Formula II:

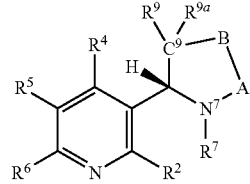

(II)

wherein A, B, $R^2$, $R^4$, $R^5$, $R^6$, $R^7$, $R^9$, and $R^{9a}$ are as described above. The method comprises oxidizing a compound of Formula I as described above in an organic solvent such as toluene to produce a compound of Formula II. The oxidizing step may be carried out with any suitable oxidizing agent, including but not limited to air, sulfur, nitric acid, $KMnO_4$, eerie ammonium nitrate, chloranil and 2,3-dichloro-5,6-dicyano-1,4-benzoquinone. The time and temperature of the oxidizing step is not critical and will usually depend upon the particular oxidizing agent used, but may be from one hour to two to four days, and a temperature between room temperature and 150° C. (e.g., by refluxing in toluene). The method may be utilized to produce enantiomerically pure C4-substituted nicotine analogs, e.g., compounds of Formula II, particularly compounds in which $R^4$ is different from at least one, two, or all three of $R^2$, $R^5$ and $R^6$. One embodiment is enantiomerically pure compounds subject to the proviso that $R^4$ is different from at least one, two, or all three of $R^2$, $R^5$ and $R^6$; another embodiment is enantiomerically pure compounds of Formula II wherein $R^4$ is $SiR^{20}R^{21}R^{22}$, wherein $R^{20}$, $R^{21}$ and $R^{22}$ are each independently selected from the group consisting of alkyl, alkenyl, alkynyl and aryl; wherein A, B, $R^2$, $R^5$, $R^6$, $R^7$, $R^9$, and $R^{9a}$ are as described above.

The invention further provides a method of making a compound of Formula III:

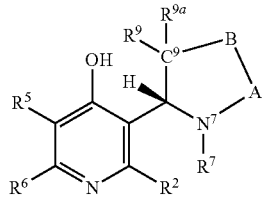

(III)

wherein:

A, B, $R^2$, $R^5$, $R^6$, $R^7$, $R^9$, and $R^{9a}$ are as described above;

the method comprises oxidizing a compound of Formula II as described above, where $R^4$ is $SiR^{20}R^{21}R^{22}$, to produce a compound of Formula III. The oxidizing step is preferably carried out in a polar protic solvent to produce a compound of Formula III. Example solvents include but are not limited to methanol, ethanol, propanol, and butanol, including mixtures thereof. The oxidizing step is preferably carried out with a peroxide oxidizing agent such as hydrogen peroxide in the presence of fluoride, which may be provided by any suitable fluoride source such as $KHF_2$. The time and temperature of the reaction is not critical, but in general may be from 1-24 hours, and may conveniently be carried out at a temperature between room temperature and 100° C. Enantiomerically pure compounds of Formula III which can be produced by such processes are also an aspect of the invention, as noted above.

Utility. Compounds of the present invention are useful in the manners described in U.S. Pat. Nos. 5,594,011 to McDonald et al. and 5,723,477 to McDonald et al. In summary, methods and intermediates of the present invention are useful for producing pharmacologically and pharmaceutically active compounds, including compounds useful for the treatment of neurological disorders such as Parkinson's disease, Alzheimer's disease, motor dynsfunction and cognitive impairment in human and animal subjects (particularly mammalian subjects such as dogs, cats, and non-human primates), as well as compounds for use as an alternative to nicotine as an aid to smoking cessation programs, as insecticides, etc. Dosage of the compound may be determined in accordance with standard techniques, but in some embodiments will be from 0.001 or 0.05 mg/kg/day, up to about 10 or 100 mg/kg/day.

The compounds disclosed herein can be prepared in the form of their pharmaceutically acceptable salts. Pharmaceutically acceptable salts are salts that retain the desired biological activity of the parent compound and do not impart undesired toxicological effects. Examples of such salts are acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like.

The compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of the invention, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and in some embodiments contain from 0.1 to 0.2 M active ingredient.

The present invention is explained in greater detail in the following non-limiting Examples.

Example 1

Preparation of 1-[4-(Dimethylphenylsilanyl)-3-(1-methylpyrrolidin-2-yl)-4H-pyridin-1-yl]-2,2-dimethylpropan-1-one (I)

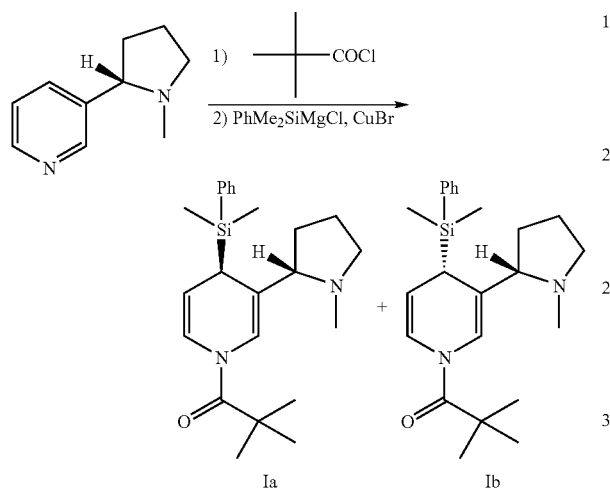

First a solution of (dimethylphenylsilyl)magnesium bromide (4 mmol) in THF was prepared according to our previous procedure and cooled to −78° C. A solution of CuBr.SMe$_2$ (0.4 g, 2 mmol) in 4 mL of diisopropyl sulfide was added dropwise to the solution of the Grignard reagent prepared above. The resulting solution was then stirred at −78° C. for 30 min during which time it turned brown-orange. In the meantime, a solution of nicotine (0.16 mL, 1 mmol) in 1 mL of THF was cooled to 0° C. and was treated with pivaloyl chloride (0.12 mL, 1 mmol). The salt was stirred at 0° C. for 1.5 h. It was then cooled to −78° C. and the solution of cuprate prepared above was injected via a double tipped needle surrounded by dry ice. The reaction mixture was then stirred at −78° C. for 4 h and then at −30° C. overnight. After warming to room temperature, the mixture was quenched with a saturated aqueous solution of NH$_4$Cl. The aqueous phase was extracted 3 times with ether. The combined organic layers were washed 3 times with 20% NH$_4$Cl/NH$_4$OH (50:50), 1 time with water, one time with brine and then dried over K$_2$CO$_3$. The solvent was removed under reduced pressure to afford 0.6 g of crude material. Purification by radial PLC (5% EtOAc/hexanes) yielded 0.312 g (81%) of product I as a mixture of diastereomers and 0.04 g (25%) of nicotine. The diastereomers were separated by RPLC (hexanes) and the de was determined to be 68%.

Diastereomer Ia: IR (neat) 2960, 1649, 1321, 1115, 814 cm$^{-1}$; $^1$H NMR (400 MHz, CDCl$_3$) δ 7.49-7.29 (m, 6H), 6.97 (s, 1H), 4.99 (dd, 1H, J=5.6 and 7.2 Hz), 2.99 (t, 1H, J=7.2 Hz), 2.36 (d, 1H, J=5.6 Hz), 2.31 (t, 1H, J=8 Hz), 2.15 (s, 3H), 2.06-1.00 (m, 14H), 0.35-0.29 (m, 6H); $^{13}$C NMR (100 MHz, CDCl$_3$) δ 172.4, 148.7, 146.4, 133.1, 133.5, 129.1, 128.9, 127.6, 127.4, 123.7, 118.6, 110.2, 68.1, 66.8, 56.6, 40.8, 38.7, 35.4, 32.1, 30.1, 27.6, −1.5, −1.6. HRMS Calcd for C$_{23}$H$_{34}$N$_2$OSi: 383.2519 [M+H]$^+$. Found: 383.2520 [M+H]$^+$. [α]$_D^{25}$ −67.3 (c 4, CH$_2$Cl$_2$).

Diastereomer Ib: IR (neat) 2960, 1849, 1321 cm$^{-1}$; $^1$H NMR (400 MHz, CDCl$_3$) δ 7.51-7.29 (m, 6H), 6.86 (s, 1H), 4.97 (t, 1H, J=6.6 Hz), 3.75-3.1 (m, 2H), 2.88 (t, 1H, J=6.4 Hz), 2.45-1.57 (m, 8H), 1.27 (s, 9H), 0.35 (s, 3H), 0.31 (s, 3H); $^{13}$C NMR (100 MHz, CDCl$_3$) δ 172.6, 149.0, 146.7, 137.7, 133.9, 133.8, 128.8, 127.8, 127.6, 127.4, 111.5, 69.5, 56.5, 56.1, 40.3, 39.8, 39.0, 27.7, 27.5, 22.9, 22.4, −1.3, −1.4; HRMS Calcd for C$_{23}$H$_{34}$N$_2$OSi: 383.2519 [M+H]$^+$. Found: 383.2520 [M+H]$^+$. [α]$_D^{25}$ +23.8 (c 7, CH$_2$Cl$_2$).

Example 2

Preparation of 4-(Dimethylphenylsilanyl)-3-(1-methylpyrrolidin-2-yl)pyridine (II)

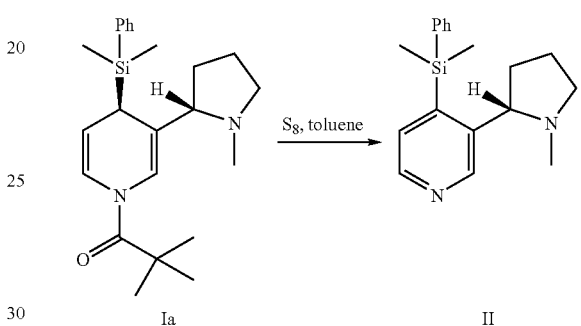

To a solution of I (1 g, 2.6 mmol) in 80 mL of toluene was added sublimed sulfur (0.09 g, 2.6 mmol). The reaction mixture was stirred and heated at 90° C. for 2 days. Evaporation of the solvent under reduced pressure afforded 1.11 g of crude product. Purification by radial PLC (5% EtOAc/hexanes) yielded 0.6 g (76%) of product II as a yellow oil. IR (neat) 2950, 2774, 1579, 1427, 1251 cm$^{-1}$; $^1$H NMR (400 MHz, CDCl$_3$) δ 8.72 (s, 1H), 8.27 (d, 1H, J=6.8 Hz), 7.31-7.13 (m, 6H), 3.03 (t, 1H, J=10.8 Hz), 2.95-2.90 (m, 1H), 1.97-1.86 (m, 2H), 1.69 (s, 3H); $^{13}$C NMR (100 MHz, CDCl$_3$) δ 148.6, 146.2, 145.4, 144.3, 137.0, 133.5, 132.6, 128.9, 128.0, 127.5, 127.1, 68.0, 56.0, 39.4, 35.3, 22.1, −1.69, −1.74. HRMS Calcd for C$_{18}$H$_{24}$N$_2$Si: 297.1787 [M+H]$^+$. Found: 297.1801 [M+H]$^+$. [α]$_D^{25}$ −82.05 (c 4, CH$_2$Cl$_2$).

Example 3

Preparation of 3-(1-Methylpyrrolidin-2-yl)pyridin-4-ol (III)

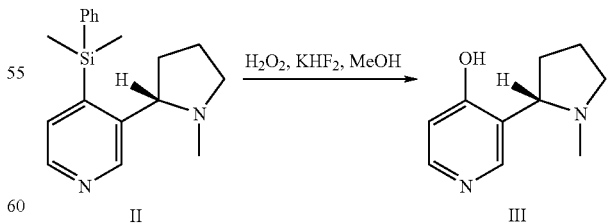

To a solution of II (0.9 g, 3.2 mmol) in 10 mL of methanol was added potassium hydrogen fluoride (0.25 g, 3.2 mmol). A solution of 30% hydrogen peroxide in water (0.88 mL, 7.7 mmol) was slowly added, and the reaction mixture was stirred and heated at 55° C. for 8 h. To the crude mixture was added K₂CO₃ until the pH of the solution became slightly basic (pH 8-9). After filtration of the solid and evaporation of the solvent, the crude product was purified by radial PLC (EtOAc) to yield 82% of III as a white solid. IR (neat) 2598, 23448, 1643 cm$^{-1}$; $^1$H NMR (300 MHz, CDCl₃) δ 8.68 (s, 1H), 8.58-8.56 (m, 1H), 8.12 (dd, 1H, J=1.5 and 8 Hz), 7.47 (dd, 1H, J=5.1 ans 8 Hz), 4.61 (dd, 1H, J=7.2 and 12 Hz), 3.79-3.59 (m, 2H), 2.94 (s, 3H), 2.72-2.1 (m, 4H); $^{13}$C NMR (75 MHz, CD₃OD) δ 170.5, 152.8, 151.4, 141.3, 124.9, 78.3, 71.4, 54.1, 29.5, 21.1. HRMS Calcd for C₁₀H₁₄N₂O: 179.1184. Found: 179.1190 [M+H]⁺. [α]$_D^{25}$: +23.8 (c=0.8, MeOH). IR (neat) 2598, 23448, 1643 cm$^{-1}$; $^1$H NMR (300 MHz,) δ 8.68 (s, 1H), 8.58-8.56 (m, 1H), 8.12 (dd, 1H, J=1.5 and 8 Hz), 7.47 (dd, 1H, J=5.1 ans 8 Hz), 4.61 (dd, 1H, J=7.2 and 12 Hz), 3.79-3.59 (m, 2H), 2.94 (s, 3H), 2.72-2.1 (m, 4H); $^{13}$C NMR (75 MHz, CD₃OD) δ 170.5, 152.8, 151.4, 141.3, 124.9, 78.3, 71.4, 54.1, 29.5, 21.1. HRMS Calcd for C₁₀H₁₄N₂O: 179.1184. Found: 179.1190 [M+H]+. [α]$_D^{25}$+23.8 (c 8, MeOH).

Example 4

3-((2S)-1-Methylpyrrolidin-2-yl)-4-phenylpyridine

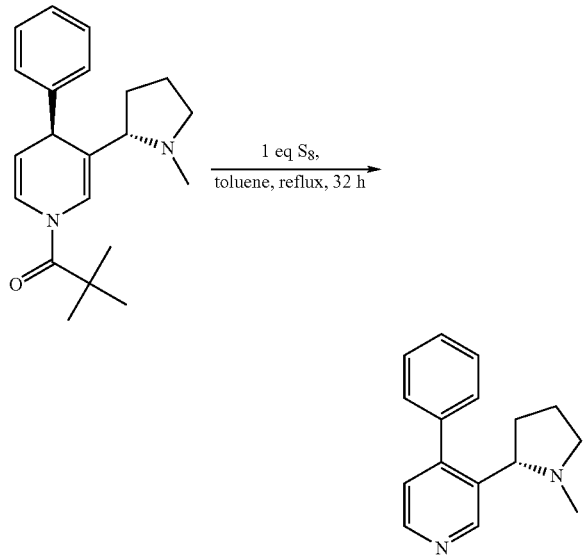

1-[(4S)-3-((2S)-1-Methylpyrrolidin-2-yl)-4-phenyl((1,4-dihydropyridyl)]-2,2-dimethylpropan-1-one (49.1 mg, 0.15 mmol) was dissolved in 2 mL of toluene. Sulfur (5 mg, 1.0 mmol) was added and the solution was refluxed for 32 h. The solution was evaporated to dryness and the residue purified by radial PLC (silica gel, 1% TEA/EtOAc) to give 21.4 mg (59%) of a white solid: mp 87-89° C.; IR (CHCl₃) 702, 843, 1042, 1004, 1473, 1587, 2779, 2966 cm$^{-1}$; $^1$H NMR (CDCl₃, 400 MHz) δ 1.80 to 1.72 (m, 2H), 2.00 to 1.88 (m, 1H), 2.08 to 2.05 (m, 1H), 2.10 (s, 3H), 2.16 to 2.12 (m, 2H), 3.17 (t, 1H, J=7.6 Hz), 7.08 (d, 1H, J=5.2 Hz), 7.26 to 7.24 (m, 2H), 7.44 to 7.43 (m, 3H), 8.49 (d, 1H, J=5.2 Hz), 8.92 (s, 1H); $^{13}$C NMR (CDCl₃, 100 MHz) δ 23.0, 35.8, 40.6, 57.0, 65.4, 124.0, 128.1, 128.5, 128.9, 139.0, 147.5, 149.8, 150.2. HRMS Calcd. for C₁₆H₁₈N₂: 239.1548. Found: 239.1561. [α]$_D^{25}$-131.5 (c 1, EtOH).

Example 5

1-[(4S)-3-((2S)-1-Methylpyrrolidin-2-yl)-4-phenyl ((1,4-dihydropyridyl)]-2,2-dimethylpropan-1-one

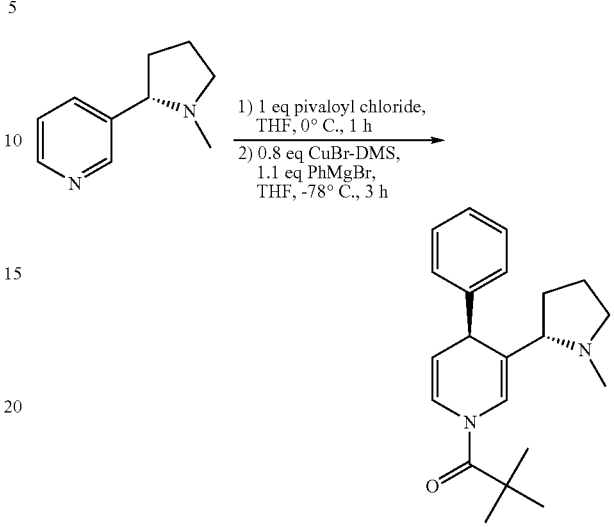

Pivaloyl chloride (0.123 mL, 1.0 mmol) was added dropwise to a solution of nicotine (0.16 mL, 1.0 mmol) in 2 mL of THF at 0° C., and the resulting solution was stirred for 1 hour to form a heterogenous mixture containing the white, solid 1-acyl pyridinium salt. Concurrently, phenylmagnesium bromide (1.1 mL, 1.1 mmol) was added slowly to a solution of CuBr.DMS (164 mg, 0.8 mmol) in 5 mL of THF at −78° C., and the resulting yellow-orange solution was stirred for 30 min. The solution was cooled to −78° C., and the organocopper reagent was added via a double tipped needle. The resulting mixture was stirred for 3 h. The reaction mixture was quenched with 2 mL of saturated NH₄Cl, and the white solid that formed was removed by vacuum filtration. The filtrate was extracted with EtOAc (3×10 mL), and the combined organic extracts were washed with 10% NH₄OH (aq) until the persistent blue color vanished from the organic phase. The organic layer was washed with saturated aqueous NaHCO₃, dried (K₂CO₃), filtered over Celite, and concentrated in vacuo. The crude yellow oil was purified by radial PLC (silica gel, 1% TEA/EtOAc) to give 245 mg (76%) of product as a light yellow solid: mp 84-85° C.; IR (CHCl₃) 2970, 2776, 1739, 1661, 1455, 1311, 1209, 1151, 1014, 968, 888, 761, 700 cm$^{-1}$; $^1$H NMR (CDCl₃, 400 MHz) δ 1.32 to 1.13 (m, 2H), 1.39 (s, 9H), 1.52 to 1.43 (m, 1H), 1.68 to 1.57 (m, 1H), 2.02 (q, 1H, J=9.6 Hz), 2.10 (s, 3H), 2.36 (t, 1H, J=8.0 Hz), 2.98 (t, 1H, J=8.8 Hz), 3.92 (d, 1H, J=4.0 Hz), 5.09 (dd, 1H, J=8.0 Hz and 4.4 Hz), 7.28 to 7.17 (m, 6H), 7.41 (s, 1H); $^{13}$C NMR (CDCl₃, 100 MHz) δ 22.8, 28.5, 34.1, 39.761, 40.7, 44.1, 56.6, 70.0, 111.4, 120.6, 123.0, 126.9, 128.5, 128.7, 145.5, 174.2. HRMS Calcd. for C₂₁H₂₈N₂O: 325.2280. Found: 325.2286. [α]$_D^{25}$−25.2 (c 1, EtOH).

Example 6

1-[3-((2S)-1-Methylpyrrolidin-2-yl)-4-methyl((1,4-dihydropyridyl)]-2,2-dimethylpropan-1-one Light yellow oil. [α]$_D^{23}$−64 (c 4.5, EtOH). IR (neat), 739, 939, 1043, 1158, 1208, 1317, 1403, 1477, 1632, 1659, 2775, 2967 cm$^{-1}$. $^1$H NMR (CDCl$_3$, 400 MHz) δ 1.11 (d, J=6.8 Hz, 3H), 1.34 (s, 9H), 1.64 to 1.86 (m, 3H), 1.88 to 1.96 (m, 1H), 2.10 (dd, J=17.2 Hz, 7.2 Hz, 1H), 2.21 (s, 3H), 2.49 (t, J=8.0 Hz, 1H), 2.89 (m, 1H), 3.09 (t, J=8.0 Hz, 1H), 5.02 (dd, J=8.4 Hz, 4.8 Hz, 1H), 7.04 (d, J=8.4 Hz, 1H), 7.15 (s, 1H). $^{13}$C NMR (CDCl$_3$, 75 MHz) δ 22.9, 23.6, 27.0, 28.4, 29.9, 23.2, 39.6, 40.8, 57.1, 70.9, 113.7, 121.4, 123.3, 124.3, 173.9. HRMS (calculated: 263.2123. found: 263.2127).

Example 7

1-[3-((2S)-1-Methylpyrrolidin-2-yl)-4-butyl((1,4-dihydropyridyl)]-2,2-dimethylpropan-1-one Light yellow oil. IR (neat) 739, 896, 928, 997, 1041, 1112, 1156, 1209, 1313, 1403, 1462, 1660, 2774, 2957 cm$^{-1}$. $^1$H NMR (CDCl$_3$, 300 MHz) δ 0.84 to 1.87 (t, J=5.1 Hz, 3H), 1.21 to 1.26 (m, 3H), 1.33 (s, 9H), 1.30 to 2.09 (m, 7H), 2.19 (s, 3H), 2.47 to 2.49 (m, 1H), 2.86 to 2.87 (m, 1H), 3.06 to 3.10 (m, 1H), 5.04 (dd, J=6.3 Hz, 3.6 Hz, 1H), 7.09 (d, J=6.0 Hz, 1H), 7.18 (s, 1H). $^{13}$C NMR (CDCl$_3$, 100 MHz) δ 14.3, 23.0, 27.4, 28.4, 32.5, 35.9, 39.6, 40.8, 57.0, 70.8, 111.7, 122.5, 123.0, 124.4, 173.9. HRMS (calculated: 305.2593. found: 305.2601).

Example 8

1-[(4S)-3-((2S)-1-Methylpyrrolidin-2-yl)-4-phenyl((1,4-dihydropyridyl)]-2,2-dimethylpropan-1-one Yellow solid, mp 84-85° C. $[α]_D^{23}$ –25.2 (c 1, EtOH). IR. (neat) 700, 762, 888, 968, 1015, 1151, 1209, 1311, 1403, 1455, 1661, 1739, 2776, 2970 cm$^{-1}$. $^1$H NMR (CDCl$_3$, 400 MHz) δ 1.12 to 1.32 (m, 2H), 1.39 (s, 9H), 1.43 to 1.52 (m, 1H), 1.57 to 1.68 (m, 1H), 2.02 (q, J=9.6H, 1H), 2.10 (s, 3H), 2.36 (t, J=8.0 Hz, 1H), 2.98 (t, J=8.8 Hz, 1H), 3.92 (d, J=4.0 Hz, 1H), 5.09 (dd, J=8.0 Hz, 4.4 Hz, 1H), 7.17 to 7.28 (m, 6H), 7.41 (s, 1H). $^{13}$C NMR (CDCl$_3$, 75 MHz) δ 22.8, 28.5, 34.1, 39.8, 40.7, 44.1, 56.6, 70.0, 111.4, 120.6, 123.0, 126.9, 128.5, 128.7, 145.5, 174.2. HRMS (calculated: 325.2280. found: 325.2286).

Example 9

1-[3-((2S)-1-Methylpyrrolidin-2-yl)-4-benzyl((1,4-dihydropyridyl)]-2,2-dimethylpropan-1-one Light yellow oil. IR (neat) 701, 742, 900, 977, 1023, 1153, 1212, 1306, 1400, 1453, 1494, 1629, 1658, 2774, 2950 cm$^{-1}$. $^1$H NMR (CDCl$_3$, 300 MHz) δ 1.33 (s, 9H), 1.75 to 2.01 (m, 4H), 2.13 to 2.17 (m, 1H), 2.3 (s, 3H), 2.37 (dd, J=12.4 Hz, 2 Hz, 1H), 2.64 (t, J=7.6 Hz, 1H), 3.11 (m, 2H), 3.27 (dd, J=12.4 Hz, 8.8 Hz, 1H), 4.84 (dd, J=8.4 Hz, 3.2 Hz, 1H), 7.01 (d, J=8.0 Hz, 1H), 7.15 to 7.29 (m, 6H). $^{13}$C NMR (CDCl$_3$, 75 MHz) δ 23.4, 26.7, 28.4, 31.9, 37.3, 39.7, 40.9, 43.7, 57.1, 71.0, 111.0, 122.7, 124.2, 126.1, 128.4, 129.6, 139.8, 174.1. HRMS (calculated: 339.2436. found: 339.2447).

Example 10

3-((2S)-1-Methylpyrrolidin-2-yl)-4-butylpyridine

Clear oil. $[α]_D^{23}$ –109.8 (c 2, EtOH). IR (neat) 837, 902, 1044, 1210, 1407, 1458, 1593, 2778, 2871, 2957 cm$^{-1}$. $^1$H NMR (CDCl$_3$, 400 MHz) δ 0.94 (t, 3H, J=7.2 Hz), 1.34 to 1.42 (m, 2H), 1.51 to 1.55 (m, 2H), 1.61 to 1.69 (m, 1H), 1.78 to 1.82 (m, 1H), 1.95 to 1.97 (m, 1H), 2.17 (s, 3H), 2.19 to 2.30 (m, 2H), 2.63 (t, 2H, J=8.0 Hz), 3.25 (dt, 1H, J=8.4 Hz and 1.6 Hz), 3.32 (t, 1H, J=8.4 Hz), 7.01 (d, 1H, J=5.2 Hz), 8.34 (d, 1H, J=5.2 Hz), 8.71 (s, 1H). $^{13}$C NMR (CDCl$_3$, 100 MHz) δ 14.1, 22.9, 31.7, 33.0, 34.9, 40.8, 57.5, 65.5, 123.8, 136.8, 147.8, 149.4, 149.7. HRMS (calculated: 219.1861. found: 219.1855).

Example 11

3-((2S)-1-Methylpyrrolidin-2-yl)-4-benzylpyridine

Clear oil. $[α]_D^{23}$ –113.9 (c 2, EtOH). IR (neat) 703, 762, 1045, 1253, 1456, 1590, 1718, 2355, 2846, 2932 cm$^{-1}$. $^1$H NMR (CDCl$_3$ 400 MHz) δ 1.54 to 1.64 (m, 1H), 1.70 to 1.79 (m, 1H), 1.89 to 1.95 (m, 1H), 1.98 to 2.65 (m, 1H), 2.11 (s, 3H), 2.22 (dd, 1H, J=17.6 Hz and 8.0 Hz), 3.21 (dt, 1H, J=8.2 Hz and 2.0 Hz), 3.33 (t, 1H, J=8.0 Hz), 4.07 (s, 2H), 6.96 (d, 1H, J=5.2 Hz), 7.08 to 7.10 (m, 2H), 7.22 to 7.31 (m, 3H), 8.39 (d, 1H, J=4.8 Hz), 8.76 (s, 1H). $^{13}$C NMR (CDCl$_3$, 100 MHz) δ 22.9, 34.4, 38.0, 40.7, 57.1, 65.9, 125.0, 126.7, 128.8, 129.1, 137.4, 139.4, 147.6, 148.1, 149.8. HRMS (calculated: 253.1705. found: 253.1695).

Example 12

1-[3-((2S)-1-Methylpyrrolidin-2-yl)-4-furanyl((1,4-dihydropyridyl)]-2,2-dimethylpropan-1-one Freshly distilled furan (1.29 mL, 17.8 mmol) was added dropwise to n-BuLi (8.5 mL, 17.8 mmol) in 5 mL THF at ±20° C. and stirred for 0.5 hours. The resulting lithiate was canulated into a suspension of magnesium bromide etherate (4.6 g, 17.8 mmol) in 10 mL THF and stirred at room temperature for 1 hour. The mixture turned brown in color. Next, the Grignard reagent was added slowly to a solution of CuBr.DMS (1.73 g, 8.4 mmol) in 15 mL of THF at −78° C., and the resulting yellow-orange organocopper reagent was stirred for 30 minutes. Concurrently in a separate flask, pivaloyl chloride (985 μL, 8 mmol) was added to nicotine (1.28 mL, 8 mmol) in 5 mL of THF at 0° C., and the mixture was stirred for 1 hour to form a heterogenous mixture containing the white, solid 1-acyl pyridinium salt. The mixture was cooled to −78° C., and the organocopper reagent was added via a jacketed (dry ice) double tipped needle. The resulting mixture was stirred for 12 hours. The reaction mixture was quenched with 2 mL of saturated NH$_4$Cl, and the white solid formed was removed by vacuum filtration. The filtrate was extracted with EtOAc (3×10 mL), and the combined organic extracts were washed with 10% NH$_4$OH (aq) until the persistent blue color vanished from the organic phase. The organic layer was washed with saturated aqueous NaHCO$_3$, dried (K$_2$CO$_3$), filtered over Celite, and concentrated in vacuo. The crude yellow oil was purified by radial PLC (silica gel, 1% TEA/EtOAc) to give 1.94 g (77%) of product. $[α]_D^{25}$ –33.8 (c 2, EtOH. IR (neat) 739, 843, 1015, 1184, 1266, 1409, 1480, 1598, 1666, 2968, 3052, 3406 cm$^{-1}$. $^1$H NMR (CDCl$_3$ 300 MHz) δ 1.26 (m, 1H), 1.38 (s, 9H), 1.72 to 1.39 (m, 3H), 2.09 (q, 1H, J=9.2 Hz), 2.16 (s, 3H), 2.44 (t. 1H, J=7.6 Hz), 3.02 (t, 1H, 9.0 Hz), 4.13 (d, 1H, J=4.0 Hz), 5.04 (q, 1H, J=3.2 Hz), 6.05 (d, 1H, J=32 Hz), 6.28 (m, 1H), 7.25 (d, 1H, J=8.0 Hz), 7.30 (s, 1H), 7.39 (s, 1H); $^{13}$C NMR (CDCl$_3$, 100 MHz) δ 22.8, 27.0, 28.5, 32.9, 36.8, 39.7, 40.8, 56.8, 69.4, 106.2, 107.8, 110.6, 111.9, 118.2, 120.3, 121.0, 124.3, 141.4, 145.2, 157.1 174.2. HRMS (calculated: 315.2073. found: 315.2086).

Example 13

Preparation of 1-[4-tert-butoxymethyl-3-(1-methylpyrrolidin-2-yl)-4H-pyridin-1-yl]-2,2-dimethyl-propan-1-one

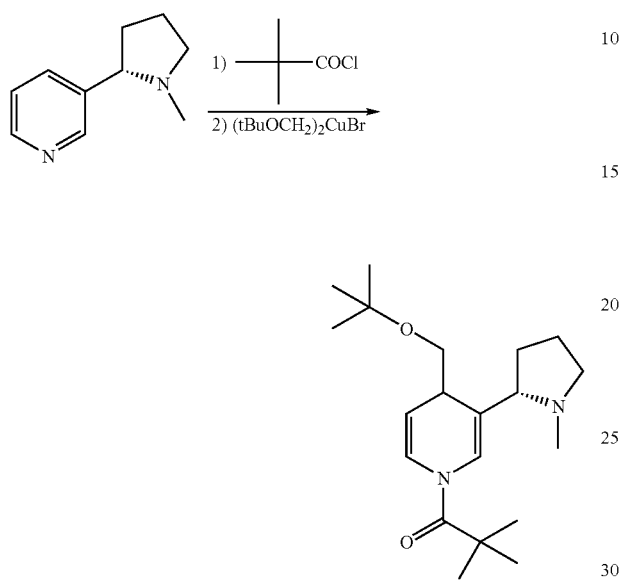

Potassium tert-butoxide (0.5 g, 4 mmol) was suspended in 16 mL of tert-butylmethyl ether (TBME). After cooling at −78° C., the well stirred mixture was treated with tert-butyllithium (3 mL, 4 mmol) over 2 min. A bright orange color was observed and stirring at −78° C. was continued for 2 h. A solution of CuBr.SMe$_2$ (0.4 g, 2 mmol) in isopropyl sulfide (3 mL) and TBME (5 mL) was slowly added. The resulting cuprate solution was stirred at −78° C. for 40 min.

In a separate flask, a solution of nicotine (0.16 mL, 1 mmol) in THF (1 mL) was cooled to 0° C. and treated with pivaloyl chloride (0.12 mL, 1 mmol). The mixture was stirred at 0° C. for 1.5 h. It was then cooled to −78° C. and treated with the cuprate solution prepared above. The reaction mixture was stirred for 3 h at −78° C. After addition of a saturated aqueous solution of NH$_4$Cl (20 mL), the aqueous layer was extracted with EtOAc (3 X). The combined organic layers were washed with 20% NH$_4$Cl/NH$_4$OH, water and brine and were dried over K$_2$CO$_3$. After evaporation of the solvent under reduced pressure, the crude material was purified by radial PLC (hexanes) to afford 0.217 g (58%) of 1-[4-tert-butoxymethyl-3-(1-methylpyrrolidin-2-yl)-4H-pyridin-1-yl]-2,2-dimethyl-propan-1-one as a yellow oil. IR (thin film, neat, NaCl) 2968, 1661, 1311 cm$^{-1}$; $^1$H NMR (CDCl$_3$, 400 MHz) δ 7.21 (s, 1H), 7.07 (d, 1H, J=8 Hz), 5.24 (dd, 1H, J=4.8 and 8 Hz), 3.58 (dd, 1H, J=4 and 8 Hz), 3.12 (t, 1H, J=8.8 Hz), 3.07-3.00 (m, 2H), 2.57 (t, 1H, J=6.8 Hz), 2.28-2.08 (m, 5H), 1.94-1.70 (m, 4H), 1.35-1.12 (m, 19H); $^{13}$C NMR (CDCl$_3$, 100 MHz) δ 173.4, 173.3, 123.7, 122.9, 119.9, 110.3, 72.3, 72.2, 70.3, 66.0, 56.6, 40.2, 39.2, 39.1, 36.2, 31.0, 28.0, 27.9, 27.3, 27.2, 22.6; HRMS Calcd for C$_{20}$H$_{34}$N$_2$O$_2$: 335.2699 [M+H]$^+$. Found: 335.2715 [M+H]$^+$. [α]$_D^{29}$ −9.6 (c 4.3, CH$_2$Cl$_2$).

Example 14

Preparation of 4-tert-butoxymethyl-3-(1-methylpyrrolidin-2-yl)-pyridine

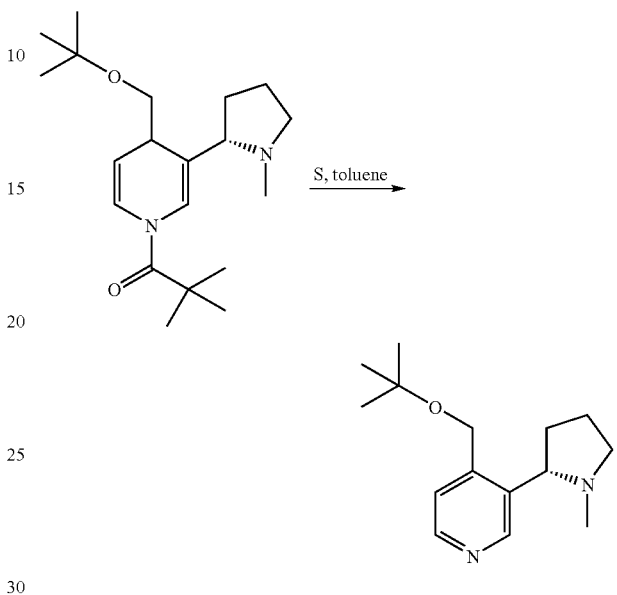

A solution of 1-[4-tert-butoxymethyl-3-(1-methylpyrrolidin-2-yl)-4H-pyridin-1-yl]-2,2-dimethyl-propan-1-one (0.194 g, 0.5 mmol), sulfur (0.02 g, 0.5 mmol) and toluene (5 mL) was refluxed for 1 day. After filtration of the mixture through a pad of Celite and evaporation of the solvent under reduced pressure, the crude material was purified by radial PLC (hexanes) to afford 0.091 g (54%) of 4-tert-butoxymethyl-3-(1-methylpyrrolidin-2-yl)-pyridine as a yellow oil. IR (thin film, neat, NaCl) 2970, 2778, 1594, 1362, 1193, 1088 cm$^{-1}$; $^1$H NMR (CDCl$_3$, 400 MHz) δ 8.72 (s, 1H), 8.45 (d, 1H, J=6.4 Hz), 7.40 (d, 1H, J=6.4 Hz), 4.52 (s, 2H), 3.32-3.20 (m, 3H), 2.32-2.22 (m, 2H), 2.18 (s, 3H), 1.96-1.66 (m, 4H), 1.29 (s, 9H); $^{13}$C NMR (CDCl$_3$, 100 MHz) δ 148.3, 147.7, 146.2, 135.3, 121.4, 73.4, 65.2, 59.6, 56.5, 40.2, 33.7, 27.20, 22.4; HRMS Calcd for C$_{15}$H$_{24}$N$_2$O: 249.1967 [M+H]$^+$. Found: 249.1964 [M+H]$^+$. [α]$_D^{28}$ −108.2 (c 3.4, CH$_2$Cl$_2$).

Example 15

Preparation of 1-[4-benzyloxymethyl-3-(1-methylpyrrolidin-2-yl)-4H-pyridin-1-yl]-2,2-dimethyl-propan-1-one

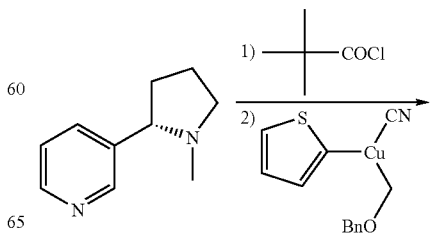

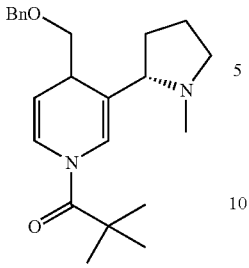

To a stirred solution of (benzyloxymethyl)tributyl stannane (prepared according to reference 1) (0.308 g, 0.75 mmol) in THF (0.75 mL) cooled at −78° C. was added n-butyllithium (0.35 mL, 0.75 mmol). After stirring at −78° C. for 30 min, the Lipshultz reagent (3 mL, 0.75 mmol) was introduced dropwise, and the mixture was allowed to stir for 30 min at −78° C. In a separate flask, a stirred solution of nicotine (0.08 mL, 0.5 mmol) in THF (1 mL) was cooled at 0° C. and treated with pivaloyl chloride (0.06 mL, 0.5 mmol). This solution was then stirred at 0° C. for 1.5 h. The cuprate solution prepared above was then transferred via a double tipped needle surrounded by a layer of dry ice to the pyridinium salt of nicotine previously cooled to −78° C. After addition of a saturated aqueous solution of NH$_4$Cl (10 mL), the aqueous layer was extracted with EtOAc (3×). The combined organic layers were washed with 20% NH$_4$Cl/NH$_4$OH, water and brine, and were dried over K$_2$CO$_3$. After evaporation of the solvent under reduced pressure, the crude material was purified by radial PLC (hexanes) to afford 0.107 g (70%) of 1-[4-benzyloxymethyl-3-(1-methylpyrrolidin-2-yl)-4H-pyridin-1-yl]-2,2-dimethyl-propan-1-one as a yellow oil. IR (thin film, neat, NaCl) 2928, 1772, 1724, 1656, 1599, 1454, 1364, 1267, 1153, 1100 cm$^{-1}$; $^1$H NMR (CDCl$_3$, 400 MHz) δ 7.01±6.94 (m, 5H), 6.80 (d, 1H, J=8 Hz), 4.93 (dd, 1H, J=4.8 Hz and 8 Hz), 4.18 (d, 2H, J=6.8 Hz), 3.37 (dd, 1H, J=4 Hz and 8.4 Hz), 3.05 (t, 1H, J=8 Hz), 2.87-2.83 (m, 1H), 2.74 (t, 1H, J=7.6 Hz), 2.25 (t, 1H, J=7.6 Hz), 1.85 (s, 3H), 1.81-1.77 (m, 1H), 1.58-1.37 (m, 4H), 1.01 (s, 9H); $^{13}$C NMR (CDCl$_3$, 100 MHz) δ 173.65, 138.51, 128.09, 127.28, 127.22, 124.40, 123.45, 119.32, 109.80, 74.32, 72.78, 70.55, 56.69, 40.32, 39.31, 35.62, 30.74, 28.06, 22.74; HRMS Calcd for C$_{23}$H$_{32}$N$_2$O$_2$: 369.2542 [M+H]$^+$. Found: 369.2543 [M+H]$^+$. [α]$_D^{28}$+26.6 (c 5.6, CH$_2$Cl$_2$). Reference 1: Kaufman, T. S. *Synlett*, 1997, 1377.

Example 16

Preparation of 4-benzyloxymethyl-3-(1-methylpyrrolidin-2-yl)-pyridine

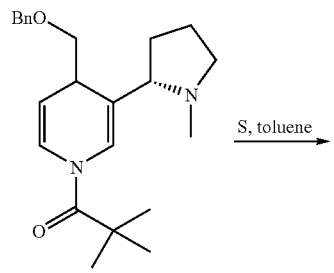

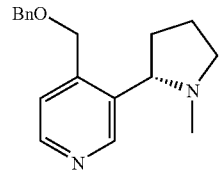

A solution of 1-[4-benzyloxymethyl-3-(1-methylpyrrolidin-2-yl)-4H-pyridin-1-yl]-2,2-dimethyl-propan-1-one (0.176 g, 0.48 mmol), sulfur (0.015 g, 0.48 mmol) and toluene (5 mL) was refluxed for 3 days. After filtration of the mixture through a pad of Celite and evaporation of the solvent under reduced pressure, the crude material was purified by radial PLC (hexanes) to afford 0.08 g (60%) of 4-benzyloxymethyl-3-(1-methylpyrrolidin-2-yl)-pyridine as a yellow oil. IR (thin film, neat, NaCl) 3436, 1637, 1090 cm$^{-1}$; $^1$H NMR (CDCl$_3$, 300 MHz) δ 8.74 (s, 1H), 8.47 (d, 1H, J=4.8 Hz), 7.40-7.27 (m, 6H), 4.62 (d, 2H, J=13.2 Hz), 3.34-3.18 (m, 2H), 2.28-2.18 (m, 2H), 2.15 (s, 3H), 2.11-1.09 (m, 5H); $^{13}$C NMR (CDCl$_3$, 75 MHz) δ 149.31, 148.37, 145.16, 137.86, 128.67, 128.06, 127.98, 122.14, 72.92, 68.19, 65.88, 57.07, 40.75, 34.28, 27.83, 22.91; HRMS Calcd for C$_{18}$H$_{22}$N$_2$O: 283.1810 [M+H]$^+$. Found: 283.1800 [M+H]$^+$. [α]$_D^{24}$−75.9 (c 2.5, CH$_2$Cl$_2$).

The foregoing is illustrative of the present invention, and is not to be construed as limiting thereof. The invention is defined by the following claims, with equivalents of the claims to be included therein.

That which is claimed is:

1. A method of making a compound of Formula III:

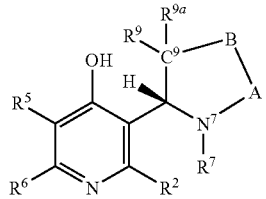

(III)

wherein:

R$^2$, R$^5$, and R$^6$ are each independently selected from the group consisting of H, alkyl, aryl, alkenyl, alkynyl, alkoxy, and halo;

R$^7$ is selected from the group consisting of H and alkyl;

A is a 1, 2 or 3 atom bridging species which forms part of a saturated or monounsaturated 5-, 6- or 7-membered ring including N$^7$, C$^8$, C$^9$ and B;

B is selected from —O—, —S—, —NR$^{10}$—, wherein R$^{10}$ is selected from hydrogen, alkyl, aryl, substituted aryl, alkylaryl, substituted alkylaryl, arylalkyl, substituted arylalkyl; —C$^{10}$HR$^{10a}$—, wherein R$^{10a}$ is selected from hydrogen, alkyl, hydroxyalkyl, aryl, aryloxyalkyl, fluoro, trifluoromethyl, cyano, cyanomethyl, —OR', —NR'$_2$, or —SR', wherein each R' is independently hydrogen, alkyl, alkenyl, alkynyl or aryl; or B is =C$^{10}$R$^{10a}$ or =N—; and R$^9$ and R$^{9a}$ are each independently selected from hydrogen, alkyl, hydroxyalkyl, aryl, aryloxyalkyl, fluoro, trifluoromethyl, cyano, cyanomethyl, —OR', —NR'$_2$, or —SR', wherein each R' is as defined above;

comprising oxidizing a compound of Formula II:

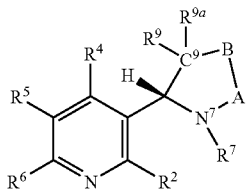

(II)

wherein A, B, $R^2$, $R^5$, $R^6$, $R^7$, $R^9$, and $R^{9a}$ are as given above and $R^4$ is $SiR^{20}R^{21}R^{22}$, wherein $R^{20}$, $R^{21}$ and $R^{22}$ are each independently selected from the group consisting of alkyl, alkenyl, alkynyl and aryl, in a polar protic solvent to produce a compound of Formula III.

2. The method of claim 1, wherein said solvent is selected from the group consisting of methanol, ethanol, propanol, and butanol.

3. The method of claim 1, wherein said oxidizing step is carried out with a peroxide in the presence of fluoride.

4. An enantiomerically pure compound of Formula III:

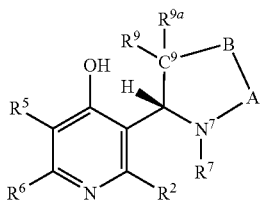

(III)

wherein:

$R^2$, $R^5$, and $R^6$ are each independently selected from the group consisting of H, alkyl, aryl, alkenyl, alkynyl, alkoxy, and halo;

$R^7$ is selected from the group consisting of H and alkyl;

A is a 1, 2 or 3 atom bridging species which forms part of a saturated or monounsaturated 5-, 6- or 7-membered ring including $N^7$, $C^8$, $C^9$ and B;

B is selected from —O—, —S—, —$NR^{10}$—, wherein $R^{10}$ is selected from hydrogen, alkyl, aryl, substituted aryl, alkylaryl, substituted alkylaryl, aryl alkyl, substituted arylalkyl; —$C^{10}HR^{10a}$—, wherein $R^{10a}$ is selected from hydrogen, alkyl, hydroxyalkyl, aryl, aryloxyalkyl, fluoro, trifluoromethyl, cyano, cyanomethyl, —OR', —NR'$_2$, or —SR', wherein each R' is independently hydrogen, alkyl, alkenyl, alkynyl or aryl; or B is =$C^{10}R^{10a}$ or =N—; and $R^9$ and $R^{9a}$ are each independently selected from hydrogen, alkyl, hydroxyalkyl, aryl, aryloxyalkyl, fluoro, trifluoromethyl, cyano, cyanomethyl, —OR', —NR'$_2$, or —SR', wherein each R' is as defined above.

* * * * *

UNITED STATES PATENT AND TRADEMARK OFFICE
CERTIFICATE OF CORRECTION

| | | |
|---|---|---|
| PATENT NO. | : 7,875,724 B2 | Page 1 of 1 |
| APPLICATION NO. | : 12/687952 | |
| DATED | : January 25, 2011 | |
| INVENTOR(S) | : King et al. | |

It is certified that error appears in the above-identified patent and that said Letters Patent is hereby corrected as shown below:

In the Specification:
Column 2, Line 32: Please correct "—$C^{10}HR^{10a}$" to read -- —$C^{10}HR^{10a}$— --

Column 7, Line 38: Please correct "formula (I)" to read -- formula (i) --

Column 16, Line 32: Please correct "at ±20°" to read -- at -20° --

In the Claims:
Column 22, Claim 4, Line 13: Please correct "aryl alkyl," to read -- arylalkyl --

Signed and Sealed this
Ninth Day of August, 2011

David J. Kappos
*Director of the United States Patent and Trademark Office*